US012559712B2

(12) United States Patent
Nagy et al.

(10) Patent No.: US 12,559,712 B2
(45) Date of Patent: *Feb. 24, 2026

(54) APPARATUS FOR PURIFYING A LIQUID COMPRISING A TARGET SUBSTANCE

(71) Applicant: Fujifilm Diosynth Biotechnologies UK Limited, Billingham (GB)

(72) Inventors: Tibor Nagy, Billingham (GB); Jonathan Haigh, Billingham (GB); Charles Heise, Billingham (GB); Andrew Topping, Billingham (GB); James Pullen, Billingham (GB)

(73) Assignee: Fujifilm Diosynth Biotechnologies UK Limited, Billingham (GB)

( * ) Notice: Subject to any disclaimer, the term of this patent is extended or adjusted under 35 U.S.C. 154(b) by 653 days.

This patent is subject to a terminal disclaimer.

(21) Appl. No.: 17/634,692

(22) PCT Filed: Aug. 6, 2020

(86) PCT No.: PCT/GB2020/051888
§ 371 (c)(1),
(2) Date: Feb. 11, 2022

(87) PCT Pub. No.: WO2021/028663
PCT Pub. Date: Feb. 18, 2021

(65) Prior Publication Data
US 2022/0325231 A1 Oct. 13, 2022

(30) Foreign Application Priority Data
Aug. 15, 2019 (GB) ...................................... 1911687

(51) Int. Cl.
*C12M 1/00* (2006.01)
*B01D 15/16* (2006.01)
(Continued)

(52) U.S. Cl.
CPC ........... *C12M 47/12* (2013.01); *B01D 15/168* (2013.01); *B01D 15/1871* (2013.01); *C07K 1/16* (2013.01); *C12M 23/58* (2013.01)

(58) Field of Classification Search
CPC ...... C12M 47/12; C12M 23/58; C12M 29/00; C12M 37/00; B01D 15/168; B01D 15/1871; B01D 15/18; C07K 1/16; C12N 15/101
(Continued)

(56) References Cited

U.S. PATENT DOCUMENTS 6,365,395 B1    4/2002  Antoniou
2018/0154280 A1  6/2018  Peyser

FOREIGN PATENT DOCUMENTS

EP    2578286 A1    4/2013
EP    2682168 A1    1/2014
(Continued)

OTHER PUBLICATIONS

Feb. 1, 20218 (WO) Written Opinion of the International Searching Authority issued in respect of International Application No. PCT/GB2020/051888.
(Continued)

*Primary Examiner* — Madeline Gonzalez
(74) *Attorney, Agent, or Firm* — Banner & Witcoff, Ltd.

(57) ABSTRACT

Apparatus for purifying a liquid comprising a target substance comprising at least two units arranged in series such that the feed stream of the second and any subsequent units comprises the product stream from a downstream unit, wherein each unit comprises specified components (i) to (vi), including a a switchable bypass assembly. Also claimed are the units and a flowpath assembly. The units may be essentially the same except for a device they contain, leading to advantages in terms of simplicity, cost and ease of (Continued)

operation, lower risk of operator error, easier maintenance and lower inventory of spare parts.

24 Claims, 2 Drawing Sheets

(51) Int. Cl.
  B01D 15/18 (2006.01)
  C07K 1/16 (2006.01)
(58) Field of Classification Search
  USPC .......... 210/634, 198.2, 650–652, 656, 416.1, 210/258, 252, 260
  See application file for complete search history.

(56) References Cited

FOREIGN PATENT DOCUMENTS

| | | | |
|---|---|---|---|
| JP | H07311188 | A | 11/1995 |
| JP | 2014509651 | A | 4/2014 |
| JP | 2017508143 | A | 3/2017 |
| WO | 2000077511 | A1 | 12/2000 |
| WO | 2012027632 | A1 | 3/2012 |
| WO | 2014085003 | A2 | 6/2014 |
| WO | WO-2015121425 | A1 * | 8/2015 ........... B01D 15/125 |
| WO | 2016025803 | A1 | 2/2016 |
| WO | 2016160157 | A1 | 10/2016 |
| WO | 2017118835 | A1 | 7/2017 |
| WO | 2018/042529 | A1 | 3/2018 |
| WO | 2019/108874 | A1 | 6/2019 |
| WO | 2019158906 | A1 | 8/2019 |

OTHER PUBLICATIONS

Feb. 8, 2022 (WO) International Preliminary Report on Patentability issued in respect of International Application No. PCT/GB2020/051888.
Oct. 10, 2023 (RU) Search Report issued in respect of RU Application No. 2022106465.
Oct. 10, 2023 (RU) Office Action issued in respect of RU Application No. 2022106465.
Mar. 6, 2024 (IN) First Examination Report in respect of IN Application No. 202217007379.
Jul. 24, 2024 (JP) Notice of Reasons for Refusal in respect of JP Application No. 2022-508998.
Jun. 28, 2024 (SG) Search Report in respect of SG Application No. 11202201314X.
Jun. 29, 2024 (SG) Written Opinion in respect of SG Application No. 11202201314X.

* cited by examiner

APPARATUS FOR PURIFYING A LIQUID COMPRISING A TARGET SUBSTANCE

RELATED APPLICATIONS

This application is a National Stage Application under 35 U.S.C. 371 of co-pending PCT application PCT/GB2020/051888 designating the United States and filed Aug. 6, 2020; which claims the benefit of GB Application number 1911687.0 and filed Aug. 15, 2019 each of which are hereby incorporated by reference in their entireties.

The present invention relates to units, flowpath assemblies and apparatus for processing liquids comprising a target substance, particularly liquids comprising a biomolecule, e.g. a recombinant polypeptide.

Many biomolecules, especially recombinant polypeptides and nucleic acids, such as plasmids (pDNA), have attracted much attention in particular for therapeutic applications. Such biomolecules are commonly produced by culturing recombinant host cells which have been engineered to express the desired biomolecule. The biomolecule is then recovered from the culture medium by methods typically comprising a number of unit operations.

Apparatus for processing a solution comprising a target substance is known in the art. However, apparatus for use in the commercial manufacture of such compounds is extremely bulky, and requires extensive floor space and infrastructure. Additionally, whilst some commonality of apparatus can be achieved for several of the unit operations, the designs of apparatus for certain unit operations, such as viral inactivation and/or ultrafiltration differ substantially from those for, for example, chromatographic purification. This means that either more space is required to accommodate two or more sets of apparatus, or that the interoperability and control of the apparatus for the stages is inordinately complex. Further, operators require training on each of the different types of apparatus employed. Accordingly, simplified and broadly-applicable apparatus would be desirable. It would also be desirable to identify apparatus enabling multiple processing steps to be carried out employing a common flow path According to a first aspect of the present invention there is provided an apparatus for converting a liquid feedstock comprising a target substance and impurities into a product stream containing purified target substance and optionally one or more waste streams comprising at least some of the impurities, the apparatus comprising at least two processing units arranged in series such that the feed stream of the second and any subsequent units comprises the product stream from a downstream unit, wherein each processing unit comprises the following components (i) to (vi):

(i) an inlet (1) for the liquid feedstock;

(ii) a multiple inlet flow-controller (4) comprising two or more variable flow inlet valves (4a) for providing at least two liquids in a desired ratio;

(iii) a mixing means (8);

(iv) a device (12) for performing a processing operation which separates at least some of the impurities from the target substance;

(v) a means (6) for imparting the flow of liquids through the unit; and (vi) a switchable bypass assembly (31) for causing liquids passing through the unit to either flow into the mixing means (8) or bypass the mixing means (8).

The present invention provides an apparatus which may be performed on a manufacturing scale and offers many advantages over prior apparatus, particularly in terms of simplicity, cost and ease of operation, lower risk of operator error, easier maintenance and lower inventory of spare parts.

In this specification the phrase "processing unit" is often abbreviated to "unit" and the two are used interchangeably.

BRIEF DESCRIPTION OF THE DRAWINGS

In the accompanying drawings:

FIG. 1 is described in more detail in the Examples section below.

FIG. 2 schematically illustrates a flowpath assembly which may used in one or two or more (preferably at least half, more preferably all) of the processing units. The flowpath assembly comprises the identified components connected by tubing, e.g. tubing made of a material which can be sterilised by gamma irradiation (e.g. a plastics material) and preferably may be disposed-of after each use or cleaned and re-used. The flowpath assembly comprises six inlets (2a) to (2f) for six different liquids (e.g. buffers, acidic solutions, alkaline solutions, organic solvents etc.) and a seventh inlet (2g) for another liquid e.g. water. The six liquids pass through respective valves (3a, 3b), (3c, 3d) and (3e, 3f) to give three liquid streams made up of the six liquids in desired proportions which feed into the multiple inlet flow-controller (4). In this embodiment the flowpath assembly further comprises a fourth tube fitted with valve (3g) for introducing an additional liquid (from inlet (2g)) into the multiple inlet flow-controller (4) (e.g. water). The inlet (1) fitted with valve (3) has a non-return valve (3h) which may be used for introducing the liquid feedstock comprising a target substance (e.g. a monoclonal antibody) and impurities into the flowpath assembly. Downstream of the multiple inlet flow-controller (4) the liquid stream passes through the means (6) for imparting flow of the liquids (e.g. an impeller blade or pump head which may be attached to a motor located external to the flowpath), the block for pressure sensor (7) and then into a switchable bypass assembly (31). The switchable bypass assembly (31) has three connections, one leading into the mixing means (8) fitted with a bubble trap, one leading out of the mixing means (8) and one leading to the inlet (12a) for the device feed. After flowing through the device (12) for achieving a processing operation (device (12) is not shown in FIG. 2) the purified liquid feedstock passes through the outlet (12b) and through the combined pressure sensor, pH and UV sensor (32). Finally the purified liquid feedstock passes through an outlet line comprising a series of valves (17), (19) and (20), which enable the flow to be controlled between an exit feed outlet, (18), a waste stream outlet, (21), and a product stream outlet, (22), The flowpath assembly comprising components (i) to (iii), (v) and (vi) as defined above in relation to the units forms a further feature of the present invention, as does the unit comprising components (i) to (vi) and units comprising the flowpath assembly and component (iv).

Figure 1:
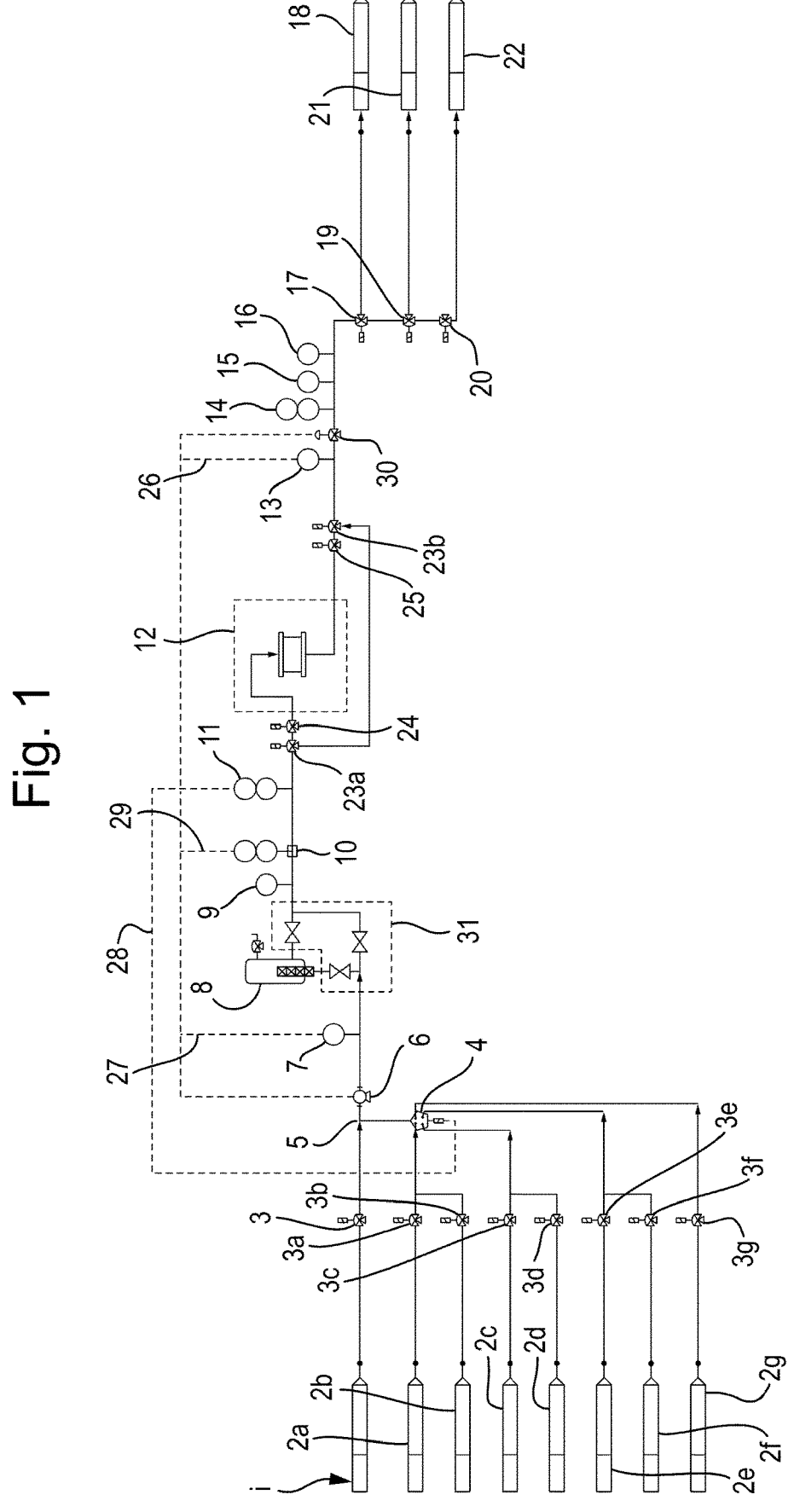
FIG. 1 is a schematic view of one processing unit which may be in the apparatus of the present invention.

Each unit typically performs one processing operation.

The number of processing units is not particularly limited and depends to a large extent of the purification steps required to convert the liquid feedstock into a form suitable for a desired purpose, for example for formulation into a medicament. In some embodiments, the apparatus comprises two units (e.g. for performing two processing operations). In other embodiments, the apparatus comprises more than two units, for example (at least) three, four, five, six, seven, eight, nine or more units, preferably each unit having the features (i) to (vi) described above.

Although the apparatus may further comprise two or more units which operate in parallel, it is preferred that all of the units are arranged in series (e.g. connected in series, optionally with a break bag between each unit if desired). In many highly preferred embodiments, the process operation performed in each unit differs from the process operation used in all of the other units. Thus although the apparatus may contain, for example, more than one unit for performing chromatography, each such chromatography unit (or the way it is used) preferably differs from the other unit(s) for performing chromatography.

In certain embodiments, each unit comprises a flowpath assembly which is substantially the same as the flowpath assembly in at least half, more preferably all, of the other units.

Preferably each unit prepares its mixed bioprocessing liquid (in situ) during operation of the apparatus. In this way, the risk of an operator using the wrong, externally-prepared bioprocessing liquid intended for a different process operation is avoided.

In certain embodiments, each unit comprises substantially the same flowpath assembly as the other units.

In one embodiment the product stream from each unit is fed directly into the next unit (when there is a next unit). In other embodiments, it is often convenient for the product stream of one more of the units to be fed into a storage vessel (e.g. a 'break bag') and then be subsequently used as the feedstock for the next unit (if any). In this way one may test the product stream before it enters the next unit, pause the process and so forth.

The feedstock for the first unit may be also be supplied from a storage vessel or, if desired, it may be supplied directly from a cell culture apparatus, e.g. a bioreactor. Examples of suitable storage vessels include tanks and bags.

The inlet (1) for the liquid feedstock typically comprises a tube, preferably fitted with a valve (3) and optionally a non-return valve (3h). The non-return valve (3h) is useful for avoiding contamination of the liquid feedstock with the liquid(s) flowing through the multiple inlet flow-controller (4). The liquid feedstock for the second and any subsequent processing units typically comprises the product from the preceding processing unit.

The multiple inlet flow-controller (4) preferably comprises variable flow inlet valves (4a), more preferably intermittent flow inlet valves, which regulate the flow of at least two liquids (e.g. 2, 3, 4, 5, 6, 7 or 8 liquids) through the multiple inlet flow-controller (4). The multiple inlet flow-controller (4) comprises at least 2 variable flow inlet valves (4a) and in many instances comprise up to 8, such as 3, 4, 5, 6 or 7, variable flow inlet valves (4a). The variable flow inlet valves (4a) may each have the same dimensions, or one or more of the variable flow inlet valves (4a) may have different dimensions. In certain preferred embodiments, the volume measured from each variable flow inlet valve (4a) to the outlet of the multiple inlet flow-controller (4) is the same for each variable flow inlet valve, and it is highly preferred that both the volume and the path length measured from each variable flow inlet valve (4a) to the outlet of the multiple inlet flow-controller (4) is the same for each variable flow inlet valve.

The multiple inlet flow-controller (4) employed in the present invention also comprises at least one outlet, and whilst two or more outlets may be present, it is preferred that a single outlet is employed.

The variable flow valves (4a) may regulate the flow between a first, relatively low flow rate wherein the liquid remains able to flow and at least a second, higher flow rate. In preferred embodiments, the variable flow inlet valve (4a) is an intermittent variable flow inlet valve which prevents flow in a first position, but permits flow in at least a second position. Most preferably, all of the valves are intermittent flow valves. The valves may comprise actuators known in the art, such as pneumatic or, preferably, solenoid actuators.

Preferably the variable flow inlet valves (4a) of the multiple inlet flow-controller (4) are controlled, most preferably by a programmable control unit, to regulate the opening and closing of these valves in order to achieve the required relative quantities of the input liquids flowing through the multiple inlet flow-controller. This is preferably achieved through cycling, with a pre-determined time period or cycle rate, through the variable flow inlet valves (4a) in the multiple inlet flow-controller (4) and regulating the opening or closing of the valve according to the required proportion of the cycle time to generate the desired composition. The cycle rate can be either constant or varied. Most preferably, intermittent flow inlet valves are employed, and are controlled such that in operation, only one valve (4a) is open at any given time. In many embodiments, the cycle rate of the multiple inlet flow-controller (4) is maintained as a constant and the desired relative quantities of the input liquids remains consistent.

In many embodiments, multiple cycles are employed. The number of cycles employed will depend on numerous factors such as the duration of the process, the volume of liquid being processed, the flow rate and the maximum operating pressure of the apparatus. In certain embodiments, at least 10 cycles, such as at least 50, 100, 500, 750, 1000, 1500, 2000, 3000, 5000, 7500, 10000 or more cycles can be employed.

It will be recognised that a range of cycle frequencies can be employed. In many instances, the frequency is less than 100 Hz, typically less than 50 Hz, commonly less than 10 Hz, and preferably less than 5 Hz. In certain preferred embodiments, the frequency is 2 Hz or less, most preferably 1 Hz or less, such as from 0.05 to 0.5 Hz.

Whilst mixing of the at least two liquids (e.g. to prepare the bioprocessing liquid or to mix a liquid with the liquid feedstock) may be achieved by simply combining the flows of the liquids through the multiple inlet flow-controller (4) outlet, optionally in combination with the action of the means (6) for imparting the flow of liquids through the unit, the unit comprises a mixing means (8), preferably a mixing chamber, preferably comprising a static mixer, most preferably a time-delay, split flow static mixer.

One of the at least two liquids is optionally the liquid feedstock.

In many embodiments, the mixing means (8) is located downstream of the means (6) for imparting the flow of liquids through the unit and upstream of the device (12) for performing a processing operation. In some preferred embodiments, the mixing means (8) comprises a bubble trap.

The mixing means (8) is preferably suitable for combining the liquid feedstock with one or more liquids to produce a device feed. The mixing means (8) is preferably also suitable for combining at least two other liquids to prepare a bioprocessing liquid.

Processing operations that can be carried out by each unit include chromatography, viral inactivation, filtration (e.g. virus removal), refolding, ultrafiltration, diafiltration, microfiltration, concentrating and/or performing buffer exchange, in-line conditioning and refolding.

In some embodiments, the apparatus comprises at least two units for performing chromatographic purification of the target substance and even, in many cases, at least three units for performing chromatographic purification of the target substance. The first unit for performing chromatographic purification of the target substance preferably comprises an affinity chromatography column. e.g. a Protein A affinity column. The second unit for performing chromatographic purification of the target substance preferably comprises anion exchange chromatography column. The third unit for performing chromatographic purification of the target substance, when present, preferably comprises a cation exchange chromatography column.

Thus in one preferred embodiment the apparatus comprises the following units arranged in series, preferably in the order listed, each unit comprising the components (i) to (vi) and with the product feed of each unit except for the final unit being used as the feedstock for the next unit:
   a. a unit for performing chromatographic purification of the target substance, preferably by affinity chromatography; and
   b. a unit for inactivation of any viruses which may be present in the liquid feedstock.

In another preferred embodiment the apparatus comprises the following units arranged in series, preferably in the order listed, each unit comprising the components (i) to (vi) and with the product feed of each unit except for the final unit being used as the feedstock for the next unit:
   a. a unit for performing chromatographic purification of the target substance, preferably by affinity chromatography;
   b. a unit for inactivation of any viruses which may be present in the liquid feedstock; and
   c. a unit for performing chromatographic purification of the target substance by cation exchange chromatography.

In another preferred embodiment the apparatus comprises the following units arranged in series, preferably in the order listed, each unit comprising the components (i) to (vi) and with the product feed of each unit except for the final unit being used as the feedstock for the next unit:
   a. a unit for performing chromatographic purification of the target substance, preferably by affinity chromatography;
   b. a unit for inactivation of any viruses which may be present in the liquid feedstock;
   c. a unit for performing chromatographic purification of the target substance by cation exchange chromatography; and
   d. a unit for performing chromatographic purification of the target substance by anion exchange chromatography.

In another preferred embodiment the apparatus comprises the following units arranged in series, preferably in the order listed, each unit comprising the components (i) to (vi) and with the product feed of each unit except for the final unit being used as the feedstock for the next unit:
   a. a unit for performing chromatographic purification of the target substance, preferably by affinity chromatography;
   b. a unit for inactivation of any viruses which may be present in the liquid feedstock;
   c. a unit for performing chromatographic purification of the target substance by cation exchange chromatography;

d. a unit for performing chromatographic purification of the target substance by anion exchange chromatography; and
   e. a unit for removal of any inactivated viruses.

In another preferred embodiment the apparatus comprises the following units arranged in series, preferably in the order listed, each unit comprising the components (i) to (vi) and with the product feed of each unit except for the final unit being used as the feedstock for the next unit:
   a. a unit for performing chromatographic purification of the target substance, preferably by affinity chromatography;
   b. a unit for inactivation of any viruses which may be present in the liquid feedstock;
   c. a unit for performing chromatographic purification of the target substance by cation exchange chromatography;
   d. a unit for performing chromatographic purification of the target substance by anion exchange chromatography;
   e. a unit for removal of any inactivated viruses: and
   f. a unit for concentrating and/or performing buffer exchange of the product stream from the preceding unit.

Preferably the units are arranged in series in the order listed herein, e.g. in an apparatus comprising units a. to g. preferably the units are arranged in series in the order a., b., c., d., e., then f.

Preferably at least one of the units (preferably at least half of the units, more preferably all of the units) further comprises a pressure sensor located upstream of component (iv).

Preferably at least one of the units (preferably at least half of the units, more preferably all of the units) further comprises a pressure sensor located downstream of component (iv).

Preferably at least one of the units (preferably at least half of the units, more preferably all of the units) further comprises a UV sensor located downstream of component (iv).

Preferably at least one of the units (preferably at least half of the units, more preferably all of the units) further comprises a pH sensor located downstream of component (iv).

Preferably at least one of the units (preferably at least half of the units, more preferably all of the units) further comprises a conductivity sensor located downstream of component (iv).

In a preferred embodiment at least 75% of the component parts of each unit other than component (iv) are identical to the component parts used in at least 80% of the other units of the apparatus. Preferably at least 85% of the component parts of each unit other than component (iv) are identical to the component parts used in at least 80% of the other units of the apparatus. Especially preferably at least 95% of the component parts of each unit other than component (iv) are identical to the component parts used in at least 80%, more preferably at least 90%, of the other units of the apparatus. In a particularly preferred embodiment, all of the component parts of each unit except for component (iv) are identical to the all of the component parts used in all of the other units of the apparatus. For the avoidance of doubt, the liquids which flow through the apparatus are not component parts of the apparatus. These embodiments are advantageous because the large degree of commonality between the component parts in each unit mean that a smaller inventory of spare parts is required. Still further, routine maintenance of the apparatus is simplified because the units are so similar and the apparatus is easier to operate (with lower risk of highly expensive target substances being destroyed) because each unit is so similar to the other units of the apparatus. In contrast to the prior art which uses very different processing units from multiple manufacturers, engineers avoid the need to learn how to service numerous very different processing units. Component (iv) in each unit typically differs from the component (iv) in other units (so that each unit can perform a discrete processing operation), hence the words "other than component (iv)".

In a preferred embodiment, all of the units of the apparatus are substantially identical except for the device (12). In this embodiment, the device (12) may be identical in two or more of the units but more typically the device (12) is different from one unit to the next, e.g. as illustrated in FIG. 1, so that each unit can perform a discrete processing operation.

The inlet for the device feed may also be used for receiving bioprocessing liquid(s), e.g. from the multiple inlet flow-controller (4) or from the mixing means (8). Bioprocessing liquids are useful for removing impurities from the liquid feedstock, e.g. as a conditioner or eluent in chromatography, as a means for inactivating viruses, as a means for washing the target substance through filters and so forth.

The apparatus optionally further comprises processing units for performing one or more of the following processing operations: chromatography, viral inactivation, filtration (e.g. ultrafiltration, microfiltration, dead end filtration and/or diafiltration), virus removal, refolding, concentrating and/or performing buffer exchange, flocculation and in-line conditioning.

Chromatography bioprocessing operations that can be performed using a device (12) include affinity chromatography (e.g. Protein A affinity chromatography), ion-exchange (either or both anion and cation exchange) chromatography, hydrophobic interaction chromatography (HIC), reverse-phase chromatography, expanded bed chromatography, mixed-mode chromatography, membrane chromatography and size exclusion chromatography (SEC). In many embodiments, at least one of the units performs the processing operation of Protein A affinity chromatography. Devices for performing chromatography operations comprise the appropriate chromatography apparatus, such as a membrane, fibre monolith or resin. The number and sequence of units performing chromatography will be selected according to the nature of the target substance.

Preferably the apparatus comprises at least two, more preferably three units comprising components (i) to (vi) for performing chromatographic purification of the target substance. In this case, the chromatographic purifications performed in each unit preferably use different conditions and/or chromatography columns packed with different materials (e.g. different resins, membranes or monoliths) to the chromatography columns to those used in all of the other units. In a particularly preferred embodiment, at least one of the unit performs affinity chromatography, at least one of the unit performs cation exchange chromatography and at least one of the unit performs anion exchange chromatography.

The device(s) (12) for performing the processing operation of viral inactivation typically comprise a storage vessel in which a liquid comprising the target substance can be stored under conditions which inactivate any viruses which are present. In certain embodiments the outlet and the inlet of the viral inactivation device (12) can be fluidly connected to generate a re-circulation loop. In one such embodiment the apparatus is set up with a vessel or bag fluidly connected between the "device" inlet and "device" outlet and one of the apparatus outlets is fluidly connected to one of the multiple inlet flow-controller (4) inlets. The vessel or bag between the device (12) "inlet" and "outlet" being fluidly connected to the liquid feedstock inlet (1) is filled by the means to impart flow (6), typically a pump, or conditioned with at least one other liquid through at least one of the other multiple inlet flow-controller (4) inlets. In certain embodiments the vessel or bag is a mixing vessel or bag. The bioprocessing liquid is re-circulated through the inlet of the multiple inlet flow-controller (4) to the vessel or bag and back to the inlet of the multiple inlet flow-controller (4) as the solution comprising the target substance is conditioned by at least one additional liquid fluidly connected to at least one other inlet on the multiple inlet flow-controller (4).

The viral inactivation may be performed by a number of techniques using conditions known in the art. For example, using a chromatography column, a chromatography membrane, or a holding tank that is capable of incubating a fluid comprising the liquid feedstock at a pH of less than about 4.0, e.g. a pH between about 3.0 to about 4.0, preferably a pH between about 3.2 to about 3.9, especially a pH between about 3.4 to about 3.8 and more especially a pH between about 3.45 to about 3.7. Preferably the liquid feedstock is held at the aforementioned pH for a period of at least 25 minutes, e.g. for a period of between about 30 minutes to 1.5 hours, preferably a period of between about 30 minutes to 1.25 hours, more preferably a period of between about 0.75 hours to 1.25 hours and especially a period of about 1 hour. In each case the conditions chosen are such that the target substance is not damaged or destroyed.

Inactivated viruses can be removed by filtration, for example using a normal flow filter (NFF) or a tangential flow filtration (TFF) filter such as is described in U.S. Pat. No. 6,365,395. In either TFF mode or NFF mode, filtration to remove inactivated viruses is conducted under conditions to retain the inactivated virus, generally using membranes having an average pore diameter of 20 to 100 nanometer (nm). Such membranes retain inactivated viruses on the membrane surface while permitting passage of the target substance through the membrane.

The unit for removing inactivated viruses may also remove any viruses which survive the virus inactivation step.

Representative suitable ultrafiltration membranes that can be used to remove inactivated viruses (along with any viruses that remain active include membranes formed from regenerated cellulose, polyethersulfone, polyarylsulphones, polysulfone, polyimide, polyamide, polyvinylidenedifluoride (PVDF) or the like and are known as VIRESOLVE® membranes and RETROPORE™ membranes available from EMD Millipore, Billerica, Mass. These can be supplied in either a cartridge (NFF) form, such as VIRESOLVE™ NFP viral filters, or as cassettes (for TFF), such as PELLICON™ cassettes, available from EMD Millipore, Billerica, Mass.

Filtration operations that can be performed using a device (12) include viral, depth and absolute filtration, ultrafiltration, diafiltration and microfiltration. In many embodiments, the filtration device (12) comprises a filter module between the device inlet and device outlet. The filter module may be flushed and chased using at least two liquid feeds attached to the multiple inlet flow-controller inlets (4) and the liquid feedstock comprising the target substance may be fluidly connected to the feedstock inlet (1). Processing of the liquid feedstock through a filtration device (12) is achieved through the means (6) for imparting the flow fluidly connected to and positioned downstream of the multiple inlet flow-controller outlet (4) and feedstock inlet (1), and upstream of the filtration device (12). The filters are often in modular form and may employ configurations which are known in the art of purifying biomolecules.

Viral filtration, depth filtration and absolute filtration process operations are known in the art and can be performed using commercially available filtration devices. In many embodiments the filtration device or devices are placed between the device (12) inlet and outlet, in order to perform filtration as the processing operation. In another embodiments an additional filter device is positioned downstream of the apparatus outlet, which in certain embodiments allows the apparatus to perform most of the purification steps, such as chromatography, viral inactivation, tangential flow filtration, viral filtration or depth filtration, followed by a secondary filtration operation external to the apparatus.

Tangential flow filtration ("TFF") unit operations that can be carried out using the apparatus of the present invention include conventional recirculating TFF and single pass TFF. In certain embodiments the outlet and the inlet of the apparatus can be fluidly connected to generate a re-circulation loop, an example being re-circulating tangential flow filtration. In one embodiment, as known in the art, the apparatus is set up with a TFF module comprising either flat sheet, hollow fibre or spiral wound membranes between the device inlet and device outlet and the retentate from the TFF module is directed from one of the apparatus outlets to a fluidly connected inlet on a vessel or bag, containing at least one inlet and one outlet. The outlet of the vessel or bag is fluidly connected to the liquid feedstock inlet. The vessel or bag is maintained at a constant level using an auxiliary means to supply the feedstock or liquid into the vessel or bag by being fluidly connected to a second inlet on the vessel or bag. In another embodiment, the apparatus is set up with a TFF module comprising either flat sheet, hollow fibre or spiral wound membranes between the device inlet and device outlet and the retentate from the TFF module is fluidly connected from one of the apparatus outlets back to one of the inlets of the multiple inlet flow-controller valve. In certain embodiments the re-circulation loop from the apparatus outlet to its inlet contains a break vessel or bag. A solution comprising a target substance or a liquid is drawn into the re-circulation loop through the liquid feedstock inlet by a means for imparting flow, typically a pump. The retentate is re-circulated through the TFF module, preferably through one of the multiple inlet flow-controller inlets. The multiple inlet flow-controller may be employed to mix the retentate with at least one other liquid. Operation of recirculating TFF is well known in the art and is controlled through setting a cross-flow rate and transmembrane pressure.

In certain embodiments single pass TFF can be configured with a TFF module comprising either flat sheet, hollow fibre or spiral wound membranes between the device inlet and device outlet for example, as in the case of single pass TFF as described in WO2017/118835.

In some embodiments a hybrid of single pass and re-circulating TFF can be employed, where the retentate generated using a variable flow valve downstream of the TFF module is returned to the feed vessel.

Apparatus according to the present invention optionally further comprises one or more of bubble traps, pressure sensors, temperatures sensors, pH sensors, flow rate sensors, conductivity sensors, air sensors, and uv sensors, such as a uv/visible multi-wavelength sensor.

Means (6) for imparting the flow of liquids are well known in the art, and include the application of gas pressure to the liquid, especially an inert gas, such as nitrogen or helium. Preferably the means for imparting the flow of liquid through a unit comprises one or more pumps. Pumps which can be employed include peristaltic, diaphragm, lobe and centrifugal pumps. Both disposable and re-usable pump designs can be employed. In many preferred embodiments, a single pump is employed for each means of carrying out a unit operation, located downstream of the fluid connection between the connection between the feedstock and the outlet from the flow-controller (4). Most preferably the pump is located upstream of the device (12). The type and size of the pump selected is commonly dependent on the flow capacity and pressure profile appropriate to the scale and design parameters of the apparatus. In certain highly preferred embodiments, the pump is a quaternary diaphragm pump.

The means (6) present in the flowpath assembly typically comprises one or more impellers, for example diaphragm impellers. These may be connected to and be driven by a means for driving the impeller, e.g. a motor located external to the flowpath assembly.

The switchable bypass assembly (31) is useful for providing the option of not allowing the liquid feedstock to enter the mixing means (8), when so desired. This provides the advantage that the device may also be used for the purification of fragile target substances where combining the liquid feedstock with a bioprocessing liquid in the mixing means (8) could or would damage or degrade the target substance.

The switchable bypass assembly (31) is also useful for mixing two or more liquids to prepare a bioprocessing liquid which may then be fed into device (12) for the processing operation.

The switchable bypass assembly (31) is particularly useful when the device (12) comprises a chromatography column. The switchable bypass assembly (31) can be used to charge the liquid feedstock contain a target substance and impurities onto a chromatography column (12) without passing through the mixing means (8) and then the mixing means (8) can be used to prepare a bioprocessing liquid (the composition of which may be altered on demand using multiple inlet flow-controller (4)) which acts as eluent for the target substance loaded on the column (12). Furthermore, it can sometimes be useful to bypass the mixing means (8) when the device (12) performs the process steps of ultrafiltration and/or diafiltration where hold-up volumes and product stability could otherwise be a problem.

The switchable bypass assembly (31) preferably comprises tubing and two or three valves which direct the flow of the liquid feedstock and bioprocessing liquids either into the mixing means (8) or to the device (12) without passing through the mixing means (8).

In one particular embodiment of the present invention, each unit comprises a flowpath assembly which comprises the following components (i) to (vi):
    (i) an inlet (1) for a liquid feedstock;
    (ii) a multiple inlet flow-controller (4) comprising two or more variable flow inlet valves (4a) for providing at least two liquids in a desired ratio;
    (iii) a mixing means (8);
    (iv) an outlet for feeding liquid to a device (12) for performing a processing operation and an inlet for receiving liquid from the device (12);
    (v) a means (6) for imparting the flow of liquids through the flowpath assembly; and
    (vi) a switchable bypass assembly (31) for causing liquids to either flow into the mixing means (8) or to bypass the mixing means (8).

This flowpath assembly forms a feature of the present invention.

On the flowpath assembly: preferably component (v) is upstream of component (iii) and downstream of component (ii); preferably component (iii) is downstream of component (ii); preferably the flowpath assembly is constructed of a plastics material; preferably the flowpath assembly is constructed of material which permits sterilisation of the assembly by gamma radiation, for example silicone, especially braided silicone, polyethylene or polypropylene; and in another embodiment the flowpath assembly is constructed of stainless steel. Preferably the flowpath assembly is sterile.

Preferably the flowpath assembly according further comprises one or more blocks for receiving a conductivity meter, pH sensor and/or a pressure sensor. Preferably at least one of the one or more blocks is located downstream of the means (6) and upstream of the mixing means (8). Furthermore, it is preferred that at least one of the one or more blocks is located downstream of the device (12). In an especially preferred embodiment at least one of the one or more blocks is located downstream of the device (12) and is adapted to receive a conductivity meter, pH meter and a pressure sensor.

Units comprising the aforementioned flowpath assembly and preferably a device (12) for performing a processing operation which separates at least some of the impurities from the target substance forms a further aspect of the present invention.

The apparatus according to the present invention preferably further comprises a means for applying additional pressure (i.e. in addition to the pressure provided by means (6) for imparting the flow) to the liquids flowing through the device (12), said means being located downstream of the device (12). Means for applying additional pressure are known in the art and include pinch valves, diaphragm valves and variable position diaphragm valves are especially preferred.

In a preferred embodiment:

(A) each unit comprises the flowpath assembly; and (B) the flowpath assembly used in at least half of the units (preferably all of the units) have substantially the same configuration.

The replaceable tubing used to make the flowpath assembly is preferably constructed from a plastics material, for example silicone, especially braided silicone.

Preferably the flowpath assembly through each unit is substantially identical to the flowpath assembly through all of the other units.

In certain embodiments, one or more of the units (preferably all of the units) comprise a multi-use flowpath assembly constructed from materials, e.g. stainless steel, that allow significant number of re-uses before replacement is required.

In certain embodiments one or more of the units (preferably all of the units) comprise a single-use flowpath assembly, preferably constructed from materials, e.g. plastics materials, that are designed with a limited lifetime and to be utilised as a disposable consumable for example silicone, especially braided silicone, polyethylene or polypropylene.

In many embodiments, each processing operation is performed under the control of a programmable control unit, preferably a computer. In some embodiments, a single control unit controls two or more processing operations. In other embodiments, each processing operation is under the control of a separate control unit. In these other embodiments, preferably the control units employ a common programming language, which enables simplified communication between control units.

In a preferred embodiment a bioprocessing liquid is provided by combining at least three liquids, at least two (preferably all) of the at least three liquids each being provided by combining at least two further liquids (e.g. using valves (3a) and (3b) or (3c) and (3d)). This combining is preferably performed in the mixing means (8). The at least three liquids may be prepared by combining the liquids (2a) and (2b), (2c) and (2d) and (2e) and (2f) respectively.

The composition of the bioprocessing liquid used in a unit may remain the same throughout the process or the composition may change during the process. For example, the composition of the bioprocessing liquid may be changed gradually or stepwise during the process, particularly when the unit comprises a chromatography column and the bioprocessing liquid acts as an eluent.

Liquids (e.g. the at least two liquids) that can be used to prepare the bioprocessing liquid include those known in the art for carrying out the appropriate processing operation. Examples of such liquids include acidic, neutral and basic solutions, for example those having a pH in the range of from 2.5 to 14 and also solutions of various salts at a variety of concentrations. Examples include aqueous solutions comprising one or more of the following: sodium potassium or ammonium hydroxide, phosphoric, sulphuric, hydrochloric or acetic acid; salts, e.g. aqueous solutions having a salt concentration of up about 3M, including sodium, calcium, potassium, and ammonium salts, for example phosphate, chloride, acetate, citrate and sulphate salts; buffers, examples of which are well known in the art; reducing agents (e.g. DTT (DL-dithiothreitol) and TCEP ((tris(2-carboxyethyl)phosphine)); amino acids (e.g. histidine, arginine and glycine); detergents (e.g. Tween™ 20 and Triton™-X100); water-miscible organic solvents, e.g. polyols, for example glycerol and polyethylene glycols; and mixtures comprising two or more of the foregoing.

Target substances which can be processed using the units, apparatus and flowpath assembly of the present invention include biomolecules, for example pDNA; cellular therapies, vaccines, e.g. viral vaccines, gene therapy products, sugars, inclusion bodies, particularly inclusion bodies comprising polypeptides; and especially recombinant polypeptides.

pDNA may be in one or more of multiple forms, such as supercoiled, linear and open-circular (i.e. nicked or relaxed) isoforms. Supercoiled pDNA isoform has a covalently closed circular form and the pDNA is negatively supercoiled in the host cell by the action of host enzyme systems. In the open-circular isoform, one strand of the pDNA duplex is broken at one or more places.

Methods for the production of pDNA are well known in the art. pDNA may be natural or artificial, for example, cloning vectors carrying foreign DNA inserts. In many embodiments, the pDNA is in the size range of 1 kilobase to 50 kilobases. For example pDNA encoding expressed interfering RNA is typically in the size range of 3 kilobases to 4 kilobases.

Polypeptides, especially recombinant polypeptides, include therapeutic proteins and peptides, including cytokines, growth factors, antibodies, antibody fragments, immunoglobulin like polypeptides, enzyme, vaccines, peptide hormones, chemokines, receptors, receptor fragments, kinases, phosphatases, isomerases, hydrolases, transcription factors and fusion polypeptides.

Antibodies include monoclonal antibodies, polyclonal antibodies and antibody fragments having biological activity, including multivalent and/or multi-specific forms of any of the foregoing.

Naturally occurring antibodies typically comprise four polypeptide chains, two identical heavy (H) chains and two identical light (L) chains inter-connected by disulfide bonds. Each heavy chain comprises a variable region ($V_H$) and a constant region ($C_H$), the $C_H$ region comprising in its native form three domains, $C_H1$, $C_H2$ and $C_H3$. Each light chain comprises a variable region ($V_L$) and a constant region comprising one domain, $C_L$.

The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Antibody fragments which can be expressed comprise a portion of an intact antibody, said portion having a desired biological activity. Antibody fragments generally include at least one antigen binding site. Examples of antibody fragments include: (i) Fab fragments having $V_L$, $C_L$, $V_H$ and $C_H1$ domains; (ii) Fab derivatives, such as a Fab' fragment having one or more cysteine residues at the C-terminus of the $C_H1$ domain, that can form bivalent fragments by disulfide bridging between two Fab derivatives; (iii) Fd fragment having $V_H$ and $C_H1$ domains; (iv) Fd derivatives, such as Fd derivatives having one or more cysteine residues at the C-terminus of the $C_H1$ domain; (v) Fv fragments having the $V_L$ and $V_H$ domains of a single arm of an antibody; (vi) single chain antibody molecules such as single chain Fv (scFv) antibodies in which the $V_L$ and $V_H$ domains are covalently linked; (vii) $V_H$ or $V_L$ domain polypeptide without constant region domains linked to another variable domain (a $V_H$ or $V_L$ domain polypeptide) that is with or without constant region domains, (e.g., $V_H$-$V_H$, $V_H$-$V_L$, or $V_L$-$V_L$) (viii) domain antibody fragments, such as fragments consisting of a $V_H$ domain, or a $V_L$ domain, and antigen-binding fragments of either $V_H$ or $V_L$ domains, such as isolated CDR regions; (ix) so-called "diabodies" comprising two antigen binding sites, for example a heavy chain variable domain ($V_H$) connected to a light chain variable domain ($V_L$), in the same polypeptide chain; and (x) so-called linear antibodies comprising a pair of tandem Fd segments which, together with complementary light chain polypeptides, form a pair of antigen binding regions.

Inclusion bodies include insoluble aggregates formed in the cytoplasm of bacterial cells such as *E. coli*, most commonly comprising polypeptide and especially recombinant polypeptide.

Methods for processing a target substance, e.g. a recombinant polypeptide, and most especially purifying or isolating a recombinant polypeptide, form further aspects of the present invention.

One embodiment of apparatus according to the present invention is described with reference to FIG. 1. A first device for performing a bioprocessing operation comprises an inlet (1) for a liquid feedstock comprising a target biomolecule and impurities and inlets (2a) to (2f) for six different buffers and an inlet (2g) for injection of water. Each inlet is fitted with a valve, such as straight-through diaphragm valve, (3) and (3a) to (3g) to enable the flow to be switched on or off. In the embodiment shown, buffer feeds passing through inlets (2a) and (2b), (2c) and (2d) and (2e) and (2f) are combined downstream of the valves, (3a) to (3f) respectively, to form three buffer feed lines, which are fluidly connected, along with the water for injection feed entering through inlet (2g) and flowing to a different inlet on a multiple inlet flow-controller, (4). The multiple inlet flow-controller, (4), comprises a four-valve manifold with a single outlet having a fast acting solenoid actuator. By this configuration, and by appropriate opening and closing of valves (3a) and (3b), (3c) and (3d), and (3e) and (3f), allows selection between buffers entering through inlets (2a) and (2b), (2c) and (2d) or (2e) and (2f), thereby increasing the flexibility of operation of the apparatus. The outlet from the multiple inlet flow-controller, (4), is in fluid connection with the inlet (1) for the liquid feedstock comprising the target biomolecule and impurities, at position (5), upstream of a pump, (6), which imparts flow of the combined feeds through a static mixer (8) fitted with a bubble trap and to the inlet of first chromatography column, (12). The line feeding the output from the pump, (6), to the chromatography column, (12), is fitted with a pressure sensor, (7), air sensor, (9), a flow meter, (10), such as an ultrasonic flow meter and a combined temperature and conductivity sensor, (11). In some embodiments, the pump, (6), is controlled via a programmable control unit in response to a feedback signal, (29), from the flow meter, (10). In some embodiments, optionally, the multiple-inlet flow controller, (4), is controlled via a programmable control unit in response to a feedback signal, (28), from the conductivity and temperature sensor, (11). The programmable control unit may also control the switchable bypass assembly (31) which provides for the liquid feedstock to enter the mixing means (8) or to bypass the mixing means (8), whichever is desired. Furthermore, the programmable control unit may also control the switchable bypass assembly (31) such that bioprocessing liquids are prepared in the mixing means (8) for onward despatch to the device (12). The outlet line from the chromatography column, (12), is provided with pressure sensor, (13), a combined temperature and conductivity sensor, (14), a uv detector, such as a uv/visible multi-wavelength detector, (15), a pH meter, (16), and a variable position valve, (30), which can be employed to regulate pressure and to impose back pressure if desired. Preferably, the operation of the pump, (6), and the variable position valve, (30), and thereby the regulation of the pressure in the apparatus, are controlled via a programmable control unit in response to feedback signals, (26) and (27), from the pressure sensors, (7) and (13). The outlet line passes through a series of valves, (17), (19) and (20), which enable the flow to be controlled between an exit feed outlet, (18), a waste stream outlet, (21), or a product stream outlet, (22), for example enabling collection or sampling. The apparatus is further fitted with valves, (23a) and (23b), which enable the flow to be diverted to bypass the column, (12), if required during operation, and further valves, (24) and (25), which enable flow through the column to be halted. The exit feed outlet, (18), can then be employed as the feed line for providing the product stream comprising a target substance and any remaining impurities from one unit to a second device for performing a further processing operation, configured as illustrated in FIG. 1, but where preferably the chromatography column, (12), is replaced with a different device (12) for performing a further processing operation, such as a different type of chromatography column, or a non-chromatographic device (12), and wherein in the second device for performing the further processing operation, the feedstock fed through inlet (1) comprises the product stream from the previous unit from product stream outlet (18).

Figure 2:
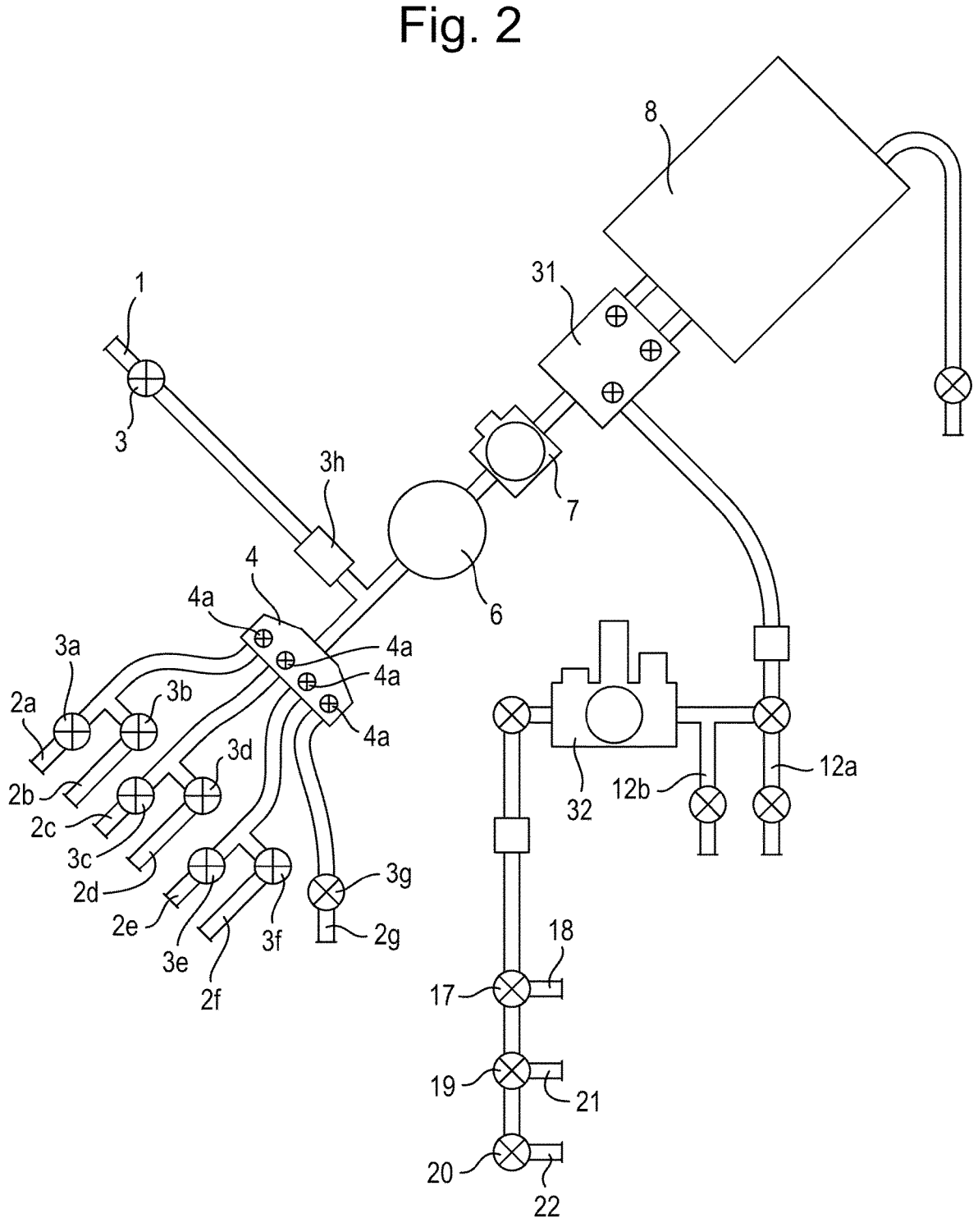
FIG. 2 schematically illustrates a flowpath assembly which may be in the units of the present invention.

In one method of operation, valve (3) is opened, whilst valves (3*a*) to (3*g*) are closed, and the liquid comprising the target substance is fed by the pump, (6), to the column, (12), to load the column with the target substance. For example, where the target substance is a monoclonal antibody, a column comprising Protein A affinity resin is preferred and the monoclonal antibody selectively binds to the Protein A resin. The switchable bypass assembly (31) allows the liquid feedstock containing the target substance and impurities to be loaded onto the column (12) without passing through the mixing means (8). On completion of the desired loading, valve (3) is closed, and one or more of valves (3*a*) to (3*g*) is opened, to enable one or more of the bioprocessing liquids enter the unit through inlets (2*a*) to (2*g*) to be pumped through the column, (12). In some embodiments, initially only valve (3*a*) is opened, and multiple-inlet valve (4) is operated so as to open the inlet valve to which buffer from inlet (2*a*), which may be a wash buffer, is supplied, such that the loaded column is washed with the buffer from inlet (2*a*). On completion of the desired washing stage, one or more of valves (3*b*) to (3*g*) may be opened, with valve (3*a*) either remaining open or being closed. The inlet valves (4*a*) on the multiple inlet valve, (4) are opened in order to allow the liquids from inlets (2*b*) to (2*g*), or mixtures thereof to be pumped through the column, (12). By controlling the opening and closing of the valves (4*a*) (the valves (4*a*) are not shown in FIG. 1 but see FIG. 2) on the multiple inlet valve, (4), and/or the valves (3*a*) to (3*g*), the composition of the bioprocessing liquid fed to the column can be altered and controlled as desired. For example, where valves (3*b*), (3*c*) and (3*e*) are open, changing the inlet valve (4*a*) which is open in the multiple-inlet flow controller, (4), and closing the others, enables the composition of the bioprocessing liquid to be changed in stepwise fashion. In another example, two or more of the inlet valves (4*a*) of the multiple-inlet flow controller, (4), can be opened and closed at a given frequency, and for a chosen period of time to enable a given mixture of the bioprocessing liquids to be fed to the column, (12). Furthermore, the switchable bypass assembly (31) allows the liquids from inlets (2*a*) to (2*g*) to be mixed in any combination or ratio in the mixing means (8) to create a bioprocessing liquid/eluent gradient which may then be fed to the column (12) pre-loaded with the target substance and impurities. Adjustment of the times and/or frequency that the inlet valves (4*a*) on the multiple inlet valve, (4), are open or closed, allows the composition of the liquid fed to the column to be altered. Where the times and/or frequency are altered in stepwise fashion, the composition also changes in a stepwise manner. Where the times and/or frequency are altered gradually over a period of time, the composition of the resultant bioprocessing liquid also changes gradually, enabling the application of a gradient to the column, (12). By whichever desired method, the composition of the bioprocessing liquid fed to the column (12) may be changed to a composition which causes the target substance to elute from the column at a different rate to the impurities and the portion of the product stream containing target substance may be collected and the waste stream either side containing impurities may be discarded. Prior to elution, liquids exiting from the column, (12) are either collected via the product stream outlet, (22), or sent to waste, (21), and valves (17), (19) and (20) are set accordingly. For elution of the target substance from the column (12), valves (19) and (20) are closed, and valve (17), opened, allowing the target substance to pass to a second processing unit through outlet (18).

Operation of the second processing unit can be substantially as described above with respect of the first unit. It will be recognised that the target substance exiting the second processing unit through the product stream outlet, (18), equivalent to the product stream outlet, (18), of the first unit, may either be recovered and used as is, or may be subject to one or more further processing operations, e.g. in further units comprising components (i) to (vi). Such further processing operations may employ conventional apparatus, or further apparatus according to the configuration illustrated in FIG. 1, or otherwise according to the present invention.

The entire subject matter of the claims is hereby incorporated into this description by reference thereto.

The present invention is illustrated without limitation by the following example.

In a chromatography process operation, a protein is bound to chromatography resin, washed with buffers of differing salt concentration and then removed (eluted) by using a high salt concentration buffer. As an example, recombinant Lactoferrin may be bound to and eluted from a 2.3 L POROS-XS cation exchange resin column using pH 7.5 sodium phosphate buffers with sodium chloride concentrations from 0 to 1 M. This may be performed on a single stand-alone unit with a fully disposable flowpath assembly that contains the features described in FIG. 1, except that valve (23*b*) is replaced with a simple fluid connection. Stock solutions are attached to the inlets in the following order: 2M sodium chloride is attached to inlet (2*a*); 0.1M dibasic sodium phosphate is attached to inlet (2*c*); 0.01M monobasic sodium phosphate is attached to inlet (2*e*); water is attached to inlet (2*g*); and the protein feed is attached to the inlet (1). Buffers are generated through proportionally selecting each of the stock solutions to produce the desired buffer composition through the action of the multiple inlet flow controller, (4), and the downstream pump, (6), and the static mixer, (8). During the establishment of the correct buffer composition, the mixing means (8) and the column, (12), are by-passed using switchable bypass assembly (31) and valve (23*a*), with valves (24) and (25) closed, the unwanted buffer being directed to the waste, (21). Once the buffer is homogeneous, as indicated by a steady reading from the upstream conductivity sensor, (11), the buffer is supplied to the chromatography column, (12), through opening valves (24) and (25) and closing the bypass line at valve (23*a*). The process conditions are monitored using the conductivity, UV and pH sensors, (14), (15) and (16), downstream of the column, (12). During the conditioning of the column ahead of the binding of the protein to the column and post-use water rinse the liquid is directed to waste, (21). Once conditioned, the chromatography resin is loaded with protein drawn in through the liquid feedstock inlet, (1), by the action of the pump, (6), pushed through the static mixer, (8), on onto the column, (12). The flowthrough from the column is collected through the exit feed, (22), whilst the first low salt buffer wash is collected through the product stream outlet, (18), and the second medium salt buffer wash was collected through the exit feed, (21). Finally, the target protein is recovered from the column using the high salt elution buffer and collected through the product stream outlet, (18).

The invention claimed is:

1. An apparatus for converting a liquid feedstock comprising a target substance and impurities into a product stream containing purified target substance and one or more waste streams comprising at least some of the impurities, the apparatus comprising at least two processing units arranged in series such that the feed stream of the second and any subsequent unit comprises the product stream from a downstream unit, wherein each processing unit comprises the following components (i) to (vi):

(i) an inlet for the liquid feedstock;

(ii) a multiple inlet flow-controller comprising two or more variable flow inlet valves for providing at least two liquids in a desired ratio;

(iii) a mixing means for combining the liquid feedstock with the at least two liquids to produce a device feed;

(iv) a device for performing a processing operation which separates at least some of the impurities from the target substance;

(v) a means for imparting the flow of the liquid feedstock and the at least two liquids through the unit; and (vi) a switchable bypass assembly for causing the liquid feedstock and the at least two liquids passing through the unit to either flow into the mixing means or bypass the mixing means, wherein each unit comprises only one means comprising a single pump located downstream of a fluid connection between the inlet and an outlet from the multiple inlet flow-controller.

2. The apparatus according to claim 1 wherein the means for imparting the flow of the liquid feedstock and the at least two liquids through the unit is located downstream of the multiple inlet flow-controller and upstream of the mixing means.

3. The apparatus according to claim 1 wherein the switchable bypass assembly comprises tubing and two or three valves which direct the flow of the liquid feedstock and/or the at least two other liquids either to the mixer means, or to the device without passing through the mixer means.

4. The apparatus according to claim 1 wherein each unit comprises a flowpath assembly in which provides for:

(a) the liquid feedstock to flow into the unit through the inlet;

(b) the at least two liquids to flow through multiple inlet flow-controller;

(c) the liquid feedstock and the at least two liquids be either mixed in the mixer means or to bypass mixer means, in either case to enter the device where a processing operation is performed which separates at least some of the impurities from the target substance to give a product stream and a waste stream; and (d) a path for the product stream, and waste stream when present, to exit the unit.

5. The apparatus according to claim 1 which comprises at least one unit comprising components (i) to (vi) for performing chromatography.

6. The apparatus according to claim 1 which comprises at least one unit comprising components (i) to (vi) for performing viral inactivation.

7. The apparatus according to claim 1 which comprises at least one unit comprising components (i) to (vi) for removing any viruses from its liquid feedstock.

8. The apparatus according to claim 1 which comprises at least two units comprising components (i) to (vi) for performing chromatography.

9. The apparatus according to claim 8 wherein the chromatographic purifications performed in each of the at least two of the units for performing the processing operation of chromatography unit use different conditions and/or chromatography columns packed with different resins to the chromatography columns to those used in the other of said units.

10. The apparatus according to claim 1 which comprises at least one unit comprising components (i) to (vi) for performing affinity chromatography, cation exchange chromatography, anion exchange chromatography, mixed-mode chromatography, hydrophobic interaction chromatography, reverse-phase chromatography, expanded bed chromatography, mixed-mode chromatography, membrane chromatography or size exclusion chromatography.

11. The apparatus according to claim 1 wherein each unit comprises a means for preparing a mixed bioprocessing liquid.

12. The apparatus according to claim 1 which comprises at least one unit comprising components (i) to (vi) for performing diafiltration of its product stream in order to buffer the target material at a pH at which the target material is stable.

13. The apparatus according to claim 1 which comprises the following units arranged in series in the order listed, each unit comprising the components (i) to (vi) and with the product feed of each unit except for the final unit being used as the feedstock for the next unit:

a. a unit for performing chromatographic purification of the target substance, preferably by affinity chromatography; and b. a unit for inactivation of any viruses which may be present in the liquid feedstock.

14. The apparatus according to claim 1 which comprises the following units arranged in series in the order listed, each unit comprising the components (i) to (vi) and with the product feed of each unit except for the final unit being used as the feedstock for the next unit:

a. a unit for performing chromatographic purification of the target substance, preferably by affinity chromatography;

b. a unit for inactivation of any viruses which may be present in the liquid feedstock; and c. a unit for performing chromatographic purification of the target substance by cation exchange chromatography.

15. The apparatus according to claim 1 which comprises the following units arranged in series in the order listed, each unit comprising the components (i) to (vi) and with the product feed of each unit except for the final unit being used as the feedstock for the next unit:

a. a unit for performing chromatographic purification of the target substance, preferably by affinity chromatography;

b. a unit for inactivation of any viruses which may be present in the liquid feedstock;

c. a unit for performing chromatographic purification of the target substance by cation exchange chromatography; and d. a unit for performing chromatographic purification of the target substance by anion exchange chromatography.

16. The apparatus according to claim 1 which comprises the following units arranged in series in the order listed, each unit comprising the components (i) to (vi) and with the product feed of each unit except for the final unit being used as the feedstock for the next unit:

a. a unit for performing chromatographic purification of the target substance, preferably by affinity chromatography;

b. a unit for inactivation of any viruses which may be present in the liquid feedstock;

c. a unit for performing chromatographic purification of the target substance by cation exchange chromatography;

d. a unit for performing chromatographic purification of the target substance by anion exchange chromatography; and e. a unit for removal of any inactivated viruses.

17. The apparatus according to claim 1 which comprises the following units arranged in series in the order listed, each unit comprising the components (i) to (v) and with the product feed of each unit except for the final unit being used as the feedstock for the next unit:

a. a unit for performing chromatographic purification of the target substance, preferably by affinity chromatography;

b. a unit for inactivation of any viruses which may be present in the liquid feedstock;

c. a unit for performing chromatographic purification of the target substance by cation exchange chromatography;

d. a unit for performing chromatographic purification of the target substance by anion exchange chromatography;

e. a unit for removal of any inactivated viruses; and f. a unit for concentrating and/or performing buffer exchange of the product stream from the preceding unit.

18. The apparatus according to claim 1 wherein:

(A) each unit comprises a flowpath assembly; and (B) the flowpath assembly used in at least half of the units have substantially the same configuration.

19. The apparatus according to claim 18 wherein the flowpath assembly is constructed from a plastics material.

20. The apparatus according to claim 18, wherein the flowpath assembly used in all of the units is substantially identical.

21. The apparatus according to claim 1 wherein at least 75% of the component parts of each unit other than the device are identical to the component parts used in at least 80% of the other units of the apparatus.

22. The apparatus according to claim 1 wherein all of the component parts of each unit except for the device are identical to the all of the component parts used in all of the other units of the apparatus.

23. The apparatus according to claim 1, which comprises a flowpath assembly comprising the following components (i) to (vi):

(i) an inlet for a liquid feedstock;

(ii) a multiple inlet flow-controller comprising two or more variable flow inlet valves for providing at least two liquids in a desired ratio;

(iii) a mixing means;

(iv) an outlet for feeding liquid to a device for performing a processing operation and an inlet for receiving liquid from the device;

(v) a means for imparting the flow of liquids through the flowpath assembly; and (vi) a switchable bypass assembly for causing liquids to either flow into the mixing means or to bypass the mixing means.

24. The apparatus according to claim 1 wherein the components (i) to (vi) are connected by tubing.

\* \* \* \* \*